United States Patent [19]

Yu

[11] Patent Number: 5,496,725
[45] Date of Patent: Mar. 5, 1996

[54] SECRETION OF CLOSTRIDIUM CELLULASE BY E. COLI

[76] Inventor: Ida K. Yu, 3202 Monte Vista Pl., Davis, Calif. 95616

[21] Appl. No.: 105,870

[22] Filed: Aug. 11, 1993

[51] Int. Cl.[6] .............................. C12N 1/15; C12N 1/21; C12N 5/10; C12N 9/42
[52] U.S. Cl. .................. 435/252.3; 435/209; 435/240.2; 435/252.33; 435/254.11; 435/320.1
[58] Field of Search ............................ 435/252.2, 252.8, 435/69.1, 842

[56] References Cited

PUBLICATIONS

Shima et al., J. Fermentation Bioeng. 68:75–78 (1989).
Gilkes et al., Biotechnology 2:259–262 (1984).
Ohmiya et al., Appl. Env. Microbiol. 55:2399–2402 (1989).
Fujino et al., J. Bacteriol. 171:4076–4079 (1989).
Yu, I. K. et al.; Abstr. Annu. Meet. Am. Soc. Microbiol., 87th Meeting, p. 272 (1987).
Shima, S.; Biol Abstr. 88(8): 84088 (1989).
Langsford, M. L. et al.; J. Gen. Microbiol. 130:1367–1376 (1984).

Primary Examiner—Robert A. Wax
Assistant Examiner—Eric Grimes
Attorney, Agent, or Firm—Albert P. Halluin; Pennie & Edmonds

[57] ABSTRACT

A gene, encoding an endocellulase from a newly isolated mesophilic Clostridium strain IY-2 which can digest bamboo fibers, cellulose, rice straw, and sawdust, was isolated by shotgun cloning in an E. coli expression plasmid pLC2833. E. coli positive clones were selected based on their ability to hydrolyze milled bamboo fibers and cellulose present in agar plates. One clone contained a 2.8 kb DNA fragment that was responsible for cellulase activity. Western blot analyses indicated that the positive clone produced a secreted cellulase with a mass of about 58,000 daltons that was identical in size to the subunit of one of the three major Clostridium cellulases. The products of cellulose digestion by this cloned cellulase were cellotetraose and soluble higher polymers. The cloned DNA contained signal sequences capable of directing the secretion of heterologous proteins from an E. coli host. The invention describes a bioprocess for the treatment of cellulosic plant materials to produce cellular growth substrates and fermentation end products suitable for production of liquid fuels, solvents, and acids.

5 Claims, 7 Drawing Sheets

SECRETION OF CLOSTRIDIUM CELLULASE BY E. COLI

SPONSORSHIP

This invention was supported in part by NSF grant PCM 84-04238 and DOE grant #DE-FG03-87ER13705.

BACKGROUND OF THE INVENTION

Cellulose is one of the most abundant carbohydrates in the plant kingdom and comprises at least one-third of the bulk of most plant tissues. In its biological cycle, cellulose is ultimately decomposed by microorganisms. Current studies of cellulases from various microorganisms are very extensive as illustrated by the ample literature in this area (See Coughlan, M. P. *Biotechnol. Genet. Eng. Rev.* 3:39–109 (1985); Saddler, J. N. *Microbiol. Sci.* 3:84–87 (1986); and Yu, I. K. and R. E. Hungate *Ann. Rech. Veter.* 10:251–254 (1979)). Several cellulase genes from Clostridium (Beguin et al., *Bio/Technol.* 1:589–594 (1983); Cornet et al., *FEMS Microbiol. Lett.* 16:137–141 (1983); and Millet et al., *FEMS Microbiol. Lett.* 29:145–149 (1985)) and other microorganisms (See Barros, M. E. C. and J. A. Thomson *J Bacteriol.* 169:1760–1762 (1987); Fukumori et al., *J. Gen. Microbiol.* 132:2329–2335 (1986); and Gilkes et al., *J. Gen. Microbiol.* 130:1377–1384 (1984)) have been cloned and sequenced (Beguin et al., *J. Bacteriol.* 162:102-1-5 (1985) and Fukumori et al., *J. Bacteriol.* 168:479–485 (1986)). It is of interest to study these enzymes from the perspective of their physiological and biochemical activity and evolution.

In spite of the extensive prior studies, most of the cellulases isolated from bacteria are not capable of digesting untreated natural materials such as bamboo fibers, plant cellulose, rice straw and sawdust. The dry matter of rice straw consists of cellulose, silica and lignin. In particular, lignocellulose, the material forming the woody cell wall of many plant tissues, cannot be hydrolyzed by most bacteria enzymes. While it has been reported that some cellulolytic fungi can degrade wood chips, their capabilities of digestion are limited to chips which have been pretreated with high pressure steam.

Some animals such as the giant panda live on bamboo as their primary diet. Since lignocellulose is known to be one of the major components of bamboo fibers, it is contemplated herein as part of the present invention that the panda may possess an unique mechanism in their digestive system by which lignocelluloses are digested and utilized as daily nutrients.

In light of the foregoing, there is a need for microorganisms capable of producing high levels of cellulases suitable for degradation of untreated natural materials such as bamboo fibers, plant cellulose, rice straw and sawdust. In addition, there is a further need to characterize such cellulases to gain an understanding of the biochemical mechanism for degradation of lignocellulose.

SUMMARY OF THE INVENTION

One aspect of the present invention involves an isolated, new mesophilic Clostridium strain IY-2 from the gut contents of the giant panda. This novel strain has demonstrated cellulase activity towards untreated natural materials such as bamboo fibers, cellulose, rice straw and sawdust. The cellulase enzyme system of this Clostridium strain IY-2 comprises at least three major cellulases with molecular masses of about 90,000 Da, 58,000 Da, and 49,000 Da, respectively. Each cellulase can hydrolyze cellulose alone but acting synergistically, they can depolymerize pebble-milled bamboo fibers, cellulose and rice straw; and digest sawdust to cellobiose, cellotetraose, and large soluble polymers of cellulose.

Another aspect of the present invention relates to the cloning of one of the endocellulase genes from this new Clostridium sp. and the expression and secretion of this cellulase by a transformed *E. coli* strain.

To achieve this end, a recombinant microorganism capable of producing cellulase for the digestion of untreated natural plant materials was successfully constructed which comprises a vector containing one or more DNA sequences coding for a cellulase gene product, and or regulatory sequences useful in the production of cellulase. In addition, to ensure that the cloned cellulase is capable of being secreted into the growth medium, one additional DNA sequence coding for a signal sequence useful for the secretion of cellulase was obtained by a shotgun cloning approach.

Preferably, the expression vector of the transformed microorganism provided by the present invention comprises a first DNA sequence coding for a cellulase obtained from a Clostridium strain IY-2 and a second DNA sequence coding for a Clostridium promoter. Thus, the *E. coli* host is capable of synthesizing and secreting extracellular cellulase at 28° C. The expression of the cellulase at 28° C. suggests that the promoter for that gene or some other promoter-like sequences that can be recognized by *E. coli* RNA polymerase have also been cloned with the cellulase structural gene. The results further suggests that *E. coli* RNA polymerase can utilize the cellulase gene's promoter to initiate transcription and subsequent expression of the clostridium cellulase in *E. coli*.

The expression plasmid of pLC2833, 2.8 kb DNA fragment which contains the cloned cellulase gene from Clostridium, is further subcloned by restriction enzyme digestion into a second plasmid containing a 2.2 kb DNA insert. The referenced 2.2 kb DNA fragment contains at least the entire structural gene of cellulase and its promoter from Clostridium strain IY-2. The plasmid which contains the 2.2 kb Clostridium DNA fragment is named pPC1A. Any microorganism which is known in the art to be amenable to the DNA mediated transformation is conceivably a target host for the present invention. A preferred host microorganism provided by the present invention is an Escherichia bacterium. Preferably, the microorganism host is *E. coli* K-12.

The invention also provides a method for producing cellulases capable of digesting untreated natural plant cellulose materials. The method comprises: (a) preparing an expression vector containing one or more DNA sequences coding for one or more gene products, signal sequences, or regulatory sequences useful in the production and secretion of cellulase; (b) transforming a host bacterium with said vector; (c) growing said transformed bacterium, in a suitable growth medium; (d) isolating said cellulase from said growth medium; and (e) incubating said cellulase with untreated natural plant materials. As described above, the expression vector provided by the present invention codes for a cellulase and a promotor/regulatory sequence/signal sequences originally obtained from the Clostridium strain IY-2.

The present invention further provides a method for the digestion of untreated natural plant materials. One generalized method comprises incubating untreated or pretreated natural plant materials with the novel cellulase enzyme of the present invention and recovering the products produced therefrom. A specific method comprises: (a) transforming a host microorganism with a vector wherein said vector containing one or more DNA sequences coding for one or more gene products, signal sequences, or regulatory sequences useful in the production and secretion of cellulase; (b) growing said transformed bacterium in a suitable growth medium; and (c) incubating the untreated natural plant materials with said growth medium. Preferably, the transformed microorganism is a Escherichia bacterium containing DNA sequences code for cellulase and its promoter obtained from a Clostridium strain IY-2. A preferred transformed strain is E. coli K-12. The untreated natural plant materials are selected from the group consisting of bamboo fibers, cellulose, rice straw or any other post-harvest agricultural plant waste. The products produced from these untreated natural plant materials consist of cellobiose, cellotetraose and larger soluble polymers of cellulose, which can be used as fermentation feed stocks for producing a variety of useful products such as ethanol, the latter of which can be produced by known or standard fermentation conditions.

The present invention further provides a method for the fermentation or cofermentation of cellulosic feed stocks with a bacterial strain containing the described DNA sequences for the production of cellobiose, cellotetralose, and other fermentation products.

Still another aspect of the present invention relates to a method for construction of a recombinant microorganism capable of secreting heterologous proteins form a host microorganism. The method involves preparing and subsequently transforming a microorganism with an expression vector containing one or more DNA sequences coding for one or more desired gene products, signal sequences, or regulatory sequences useful in the production and secretion of said heterologous proteins.

DETAILED DESCRIPTION OF THE INVENTION

The present invention relates to the isolation, cloning and expression of one of the major cellulase genes from a newly isolated Clostridium strain IY-2 into E. coli. The gene, encoding an endocellulase with xylanase activity from said mesophilic Clostridium strain IY-2, was isolated by shotgun cloning of Sau3A partially digested chromosomal DNA in an E. coli expression plasmid pLC2833. The positive clones of E. coli were selected based on their ability to hydrolyze pebble-milled bamboo fibers and cellulose present in agar plates. As a result, one clone containing a 2.8 kb DNA fragment which is responsible for cellulase activity has been identified. A 2.2 kb EcoRl-HindIII fragment that retains the cellulase activity was subcloned into plasmid vector pLC2833. The products of cellulose digestion by this cloned and secreted cellulase were cellotetraose and soluble higher polymers, which are identical to the products formed by the authentic Clostridium enzyme.

The present invention also provides for a novel cloning strategy for the expression of Clostridium cellulases. For example, it was initially believed that a controlled expression probe plasmid, pLC2833, has to be used to clone and express a cellulase gene. It was later shown that such an expression vector was not necessary for the expression of Clostridium enzyme. The cellulase gene was expressed at 28° C. and the product was not detrimental to the growth of E. coli. This is probably due to the fact that the enzyme was secreted into medium. The expression of the gene at 28° C. suggests that the promoter for the gene or some other promoter-like sequences that can be recognized by E. coli RNA polymerase have also been cloned with the structural gene and that the RNA polymerase of E. coli can utilize the cellulase gene's expression elements at 28° C.

As a result of genetic transformation provided by the present invention, the transformed E. coli not only can express the cloned gene, but also can secrete its cellulase product into the medium. This secreted cellulase has the same molecular mass and activity as enzyme II of the major cellulase originally isolated from the Clostridium strain IY-2. In addition, the subunit of the secreted enzyme has the same electrophoretic mobility, molecular size, and antigenic property as the subunit from Clostridium cellulase II. Since E. coli usually secretes protein products into the periplasmic space, but not into the medium due to the existence of an outer membrane secretion barrier, the present invention further provides an unique method for the construction of recombinant microorganism capable of producing and secreting heterologous proteins from a host microorganism. This method thus provides a convenient way to isolate extracellular cellulase and other heterologous proteins without the risks of contamination resulting from cellular extraction.

Furthermore, the amount of cellulase being produced by the genetically transformed E. coli is significantly higher than that produced by Clostridium strain IY-2. The rate of cellulase produced based on conversion of cellulose to measurable carbohydrate degradation products is approximately 30 to 50 fold higher with E. coli as with the Clostridium strain. On cellulose-agar plates the overnight halo produced around an pPC1A transformed E. coli colony is equivalent to the size of a month old Clostridium colony, thus indicating the high productivity and secretion of cellulase from the pPC1A transformed E. coli.

In addition, the substrate specificity of the cloned cellulase is particularly interesting, since it can hydrolyze native bamboo fibers, rice straw and native cellulose. The products formed were cellotetraose and soluble polymers. This is a relatively rare property for most of the cellulases that have been reported, since most tend to hydrolyze carboxymethylcellulose and not native cellulose, rice straw and bamboo fibers. Thus, with the achievement of hyperproduction of this enzyme, the present invention provides for a source of novel cellulase activity capable of digesting untreated natural materials such as bamboo fibers and cellulose, rice straw which cannot be hydrolyzed by most bacteria.

The cloned cellulase provided by the present invention may find particular utility in the waste management of the post-harvest agricultural plant materials. These materials are conventionally burned or buried by the farmers which will cause long term detrimental effects to the environment. The present invention, however, provides for a method in which these materials can be incubated either with the cloned cellulase or with a recombinant microorganism capable of secreting said cellulase for a partial or complete digestion of these materials. The digested products produced from these, or other untreated natural plant materials consist of cellobiose, cellotetraose and large soluble polymers of cellulose, which can be used as fermentation feed stocks for producing a variety of useful products such as ethanol, other liquid fuels and solvents, the latter of which can be produced by known or standard fermentation conditions.

A standard fermentation process suitable for the production of fermentation feed stocks from the untreated plant materials or post-harvest agricultural plant materials comprises incubating a culture of a recombinant microorganism capable of secreting the cloned cellulase enzyme, or alternatively, the cellulase enzyme, with these materials in a suitable medium in a fermentor having a sufficient working volume. The fermentation can be performed under a suitable temperature and pH range typically known in the art for bacterial fermentations.

The cellulase provided by the present invention can also be used as a cleaning composition in the protein detergent industry. The cellulase can be suitably formulated with other laundry additives and compositions known in the art for the detergent industry. Such formulated detergents may have an enhanced cleaning ability in removing dirts and contaminants derived from the grass or other plant materials.

The novelty of the cellulases isolated from the new Clostridium strain IY-2 was further confirmed by the cloning experiments provided by the present invention. These experiments demonstrate that both the enzyme properties and the restriction map of the fragment containing the cellulase gene are different from that reported for DNA fragments containing cellulase genes from other Clostridium species or other microorganism.

The following examples are presented to provide a better understanding of the present invention and for purposes of illustration. The examples, however, are not to be construed as limiting the invention to the precise form disclosed or to limit the scope of the invention in any manner or means.

It should be noted that the isolated and purified Clostridium strain IY-2 was used as the source for the isolation and characterization of the Clostridium cellulase gene. In addition, the E. coli K-12 and plasmid pLC2833 (Remaut, E., P. Stanssens, and W. Fiers, 1981 "Plasmid Vectors for High Efficiency Expression Controlled By The $P_L$ Promoter of coliphage Lambda" Gene, 15:81–93) containing $\lambda P_L$ promoter for controlled high expression of genes, among others, also were used in subsequent gene cloning and expression experiments described by the present invention.

EXAMPLE 1

Isolation of Clostridium Strain IY-2 and Its Cellulolytic Activity

The novel cellulase producing Clostridium strain IY-2, derived from bacteria extracted from panda gut juice, was initially isolated by screening for clearing around colonies in anaerobic tube cultures using untreated bamboo fibers (the bamboo fibers had been cut and blended in a Waring blender) as the sole carbon source (the roll tubes contained agar and the bamboo fibers). The colonies containing gram positive, spore forming, strictly anaerobic bacteria were selected. After several steps of colony purification, the pure culture was incubated with several different untreated bamboo fibers as the cellulose substrates in medium CL to obtain the novel, purified and isolated strain identified as IY-2.

Subsequently additional experiments were carried out with the isolated strain identified as IY-2. The amount of substrate utilized and the digestion products were analyzed. In these experiments the isolated and purified Clostridium strain IY-2 was grown anaerobically at 37° C. in a growth medium (CL medium) consisting of 0.05M $K_2HPO_4$, 0.05M $KH_2PO_4$, 3 mM $(NH_4)_2SO_4$, 6 mM $MgSO_4$, 6 mM NaCl, 0.05M $NaHCO_3$, 0.3M $Na_2S$, 1.5 mM cysteine-HCl, 1% cow rumen fluid, and varying amounts (usually 0.6%) of pebble-milled cellulose or other cellulosic materials including bamboo fibers at 37° C. Solid media contained 15 g agar per liter.

TABLE 1

Substrates and Products of Clostridium strain IY-2 Cellulolytic Activity

| Substrate | Time of Incubation (Days) | Total Amount of Substrate Digested (g/l of culture) | Products Observed by Thin Layer Chromatography |
|---|---|---|---|
| Cellulose (50%) + lignocellulose (50%) | 7 | 34 | Cellobiose Cellotetraose Soluble Residues |
| Sawdust | 30 | 21 | Cellotetraose Soluble Residues |
| Rice Straw | 14 | 25 | Cellobiose Cellotetraose Soluble Residues |

The results in Table I indicate that this isolate IY-2 can degrade cellulose bamboo fibers, sawdust, and rice straw. The major products which remained after growth were cellobiose, cellotetraose, and soluble polymers.

EXAMPLE 2(A)

Purification of the Clostridium Strain IY-2 Cellulases.

Figure 1:
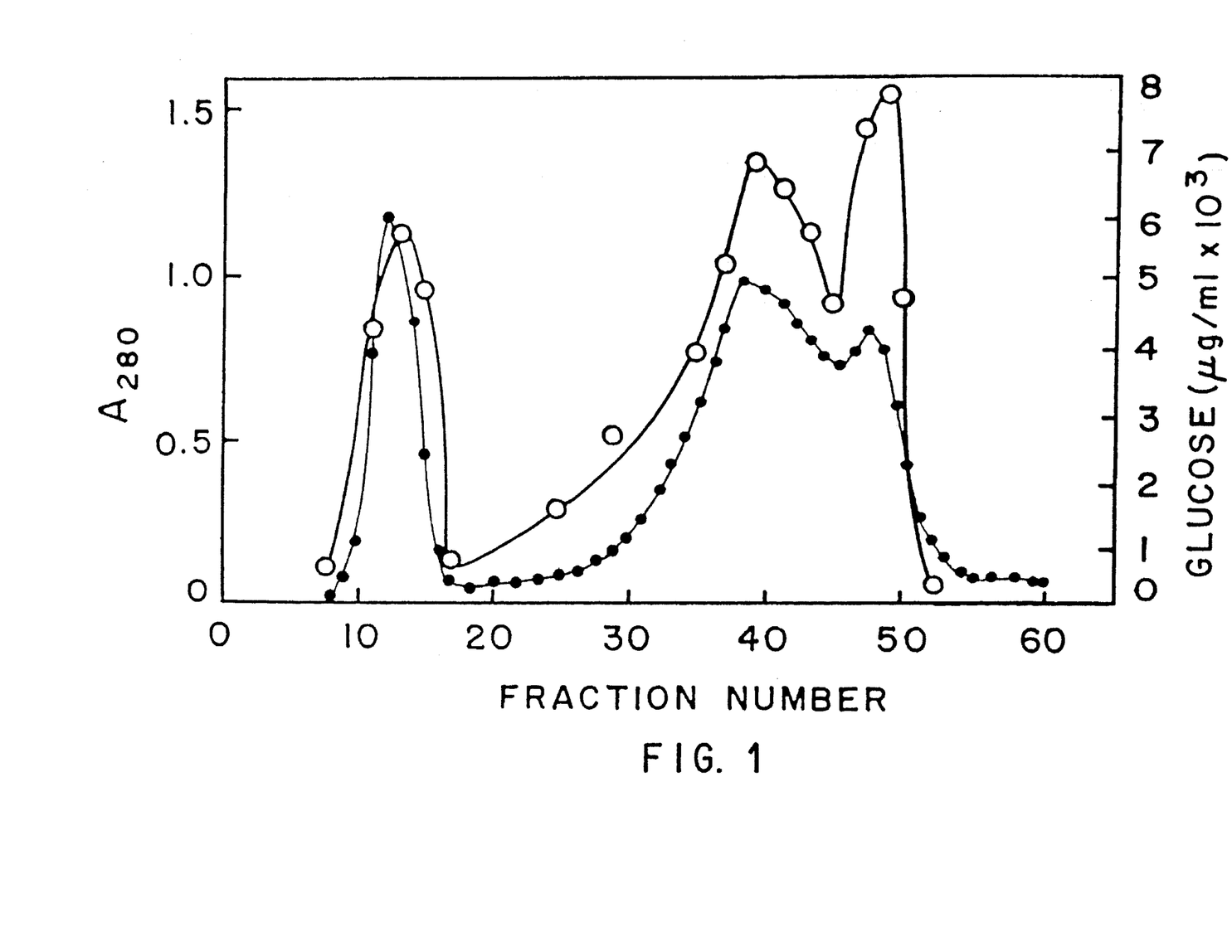
FIG. 1 shows analysis of the gel chromatographic elution pattern of the major cellulases from Clostridium strain IY-2.
Figure 2:
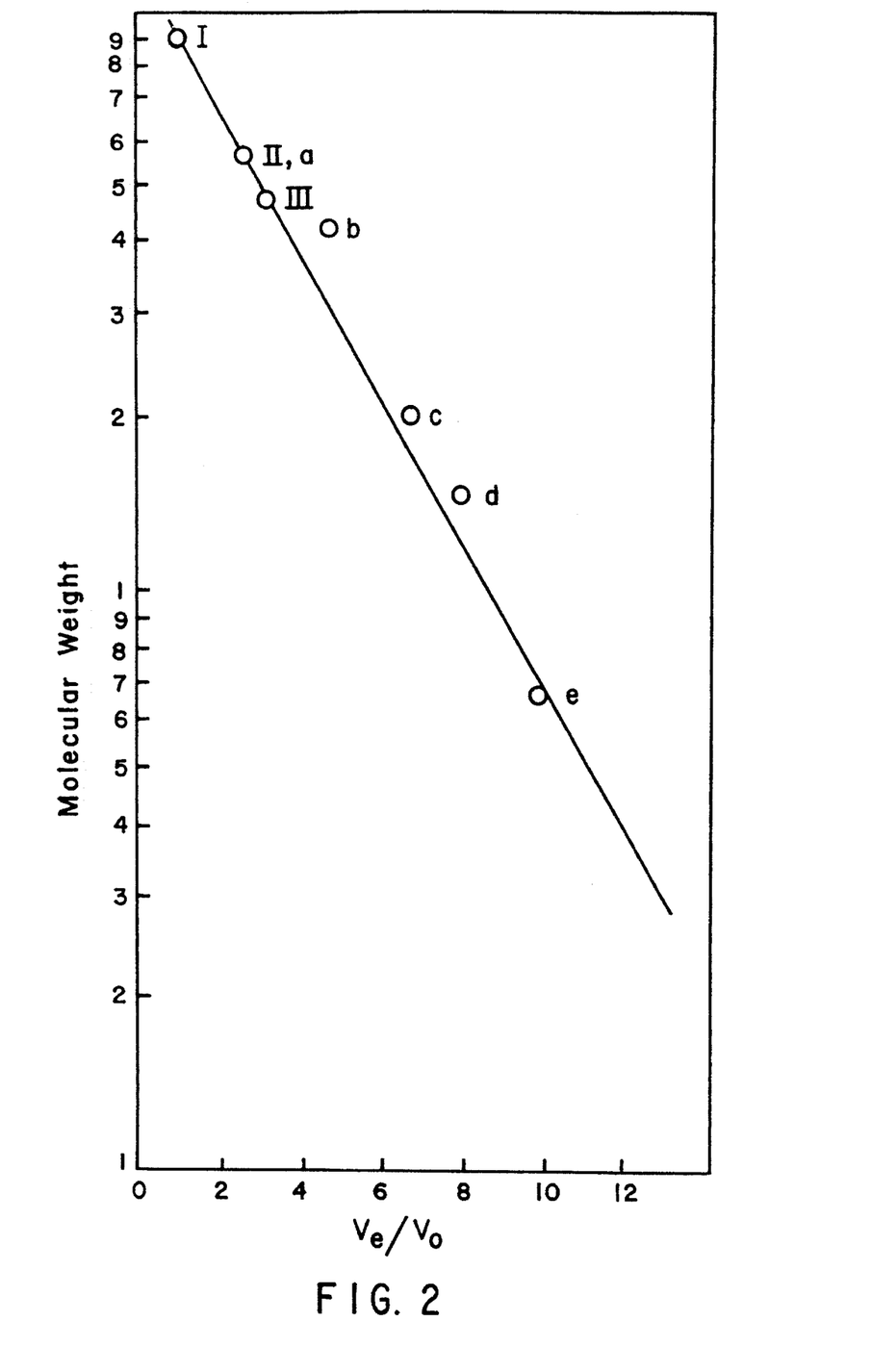
FIG. 2 shows the molecular weights of the three major cellulases determined from the elution positions of the enzymes from FIG. 1. The numbers on the left indicate the molecular weights of standard proteins$\times 10^{-3}$. I, cellulase I; II, cellulase II; III, cellulase III.

One liter of Clostridium strain IY-2 was grown to late log phase in CL medium containing 0.6% pebble-milled cellulose. The cells were removed by centrifugation, and the supernatant was filtered through a 0.45 μm Millipore filter. The supernatant containing the cellulases were concentrated by ultrafiltration (Amicon PM10 membrane) at 0° C. The final volume of concentrated enzymes was 10 to 20 ml. The enzymes were then separated by use of a Bio-Gel A 15M column (2.6×40 cm). Phosphate buffer (0.05M, pH 6.8) was used to elute the enzymes in 2.5 ml fractions. Absorbance of the eluate was measured at 280 nm. Cellulase activity of the effluent fractions was measured by the anthrone method. Trevelyan, W. E. and J. S. Harrison *J. Biochem.* 50: 298–303 (1952). Each of the enzyme peaks from the Bio-Gel column was collected according to its 280 nm absorbance and cellulase activity was determined using pebble milled Whatmann filter paper as the assay method, active fractions were then concentrated with an Amicon Diaflo UM-10 membrane under 30 psi $N_2$ pressure. Concentrated enzymes were dialyzed several times with 0.02M ethanolamine buffer, at pH 9.0. Each concentrated enzyme fraction was then further purified by passage through a DEAE-Sepharose column. The DEAE-Sepharose column (1.5×30 cm) was equilibrated with 0.02 N ethanolamine, pH 9.0, and the enzymes were eluted with an 0.1M to 0.7M NaCl gradient by collecting 1 ml fractions. Enzyme activity and absorbance was measured as above. The purity of each of the enzymes was determined by SDS- 10% polyacrylamide gel electrophoresis. As shown in FIG. 1, three major cellulase activities produced by the Clostridium strain IY-2 were characterized. The molecular weights of the enzymes as determined by Bio-Gel column elution were about 90,000 (enzyme I), 58,000 (enzyme II) and 49,000 (enzyme III) as shown in FIG. 2.

EXAMPLE 2(B)

Chromatofocusing Characterization and Determination of the pI of Cellulases.

Figure 3:
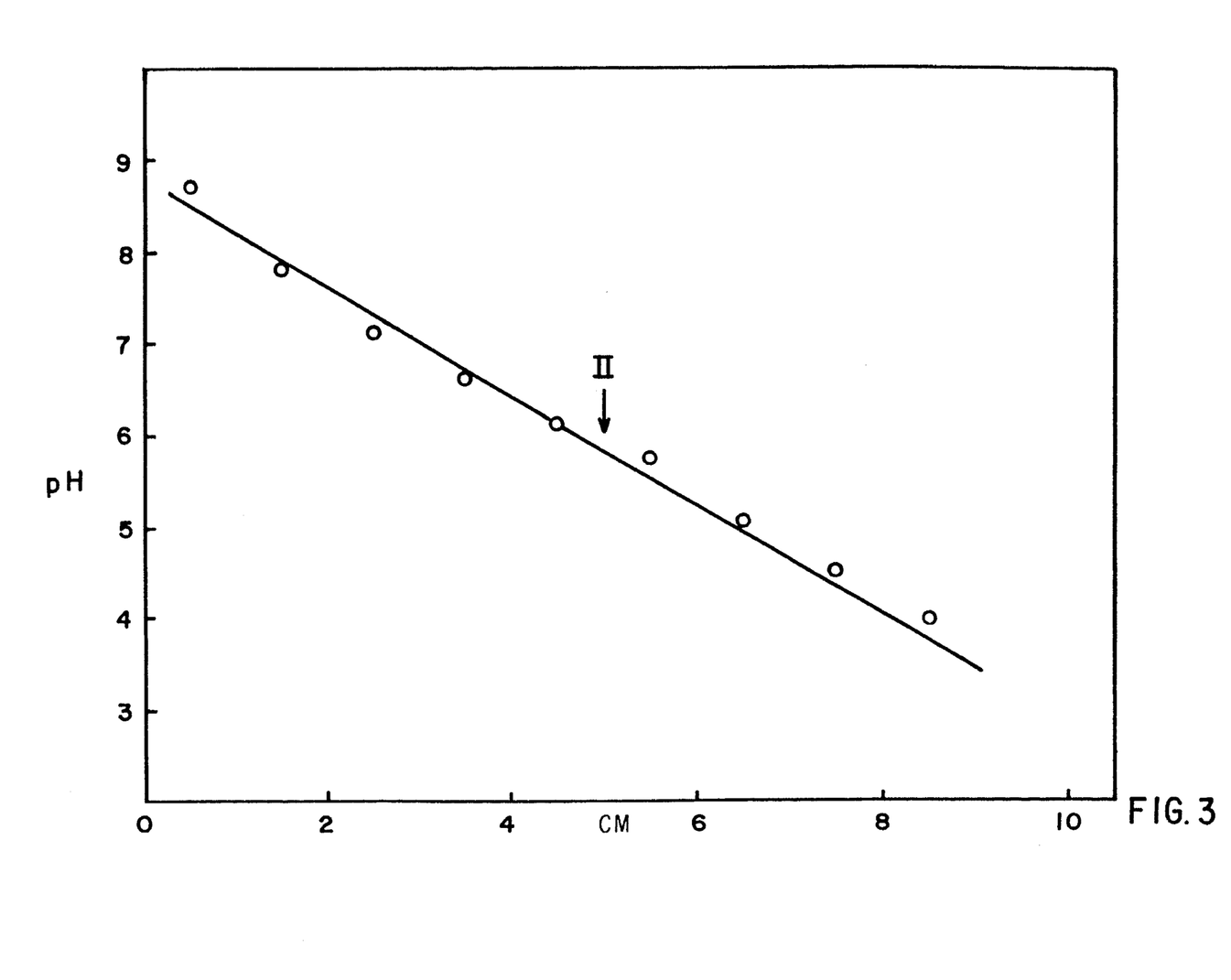
FIG. 3 shows the pI of cellulase II.

Polyacrylamide gels containing carrier ampholytes (LKB Ampholine PAK plates) for analytical electofocusing were used for the determination of the pIs of the cellulases. The anode and cathode solutions contained 0.1M glutamic acid in 0.5M $H_3PO_4$ and 0.1M β-alanine, respectively. Chromatofocusing was carried out at 10° C., 2,000 volts, 25 mA, and 25 watts for 2.5 hours. The pH gradient was determined after the run by placing a surface pH electrode on the gel at 10 positions between the anode and the cathode. The plate was stained for 1 hour using staining kit Coomassie Blue R 250. As the results shown in FIG. 3, the pIs for enzymes I, II, and III were 7.8, 5.8, and 4.35, respectively.

EXAMPLE 2(C)

Preparation of Anti-Cellulase Antiserum and Immunochemical Methods

One mg/ml of purified cellulase (containing a 1:1:1 w/w mixture of the three major cellulases) as purified in Example 2(B) was mixed with 1 ml of complete Freund's adjuvant and was injected into several locations of the backs of four month old New Zealand rabbits. Booster injections containing 1 mg of cellulase in incomplete adjuvant were given 4 and 6 weeks later. The serum was collected one week after the last injection. To remove antibodies that can cross react nonspecifically with *E. coli* proteins, the serum was diluted 10-fold with TBS buffer (20 mM Tris-HCl, pH 7.5, 0.05M NaCl) and 2% fetal calf serum. This solution was incubated with nitrocellulose membranes which had been coated with an *E. coli* lysate containing plasmid pLC2833 (Remaut, E., P. Stanssens, and W. Fiers, 1981 "Plasmid Vectors for High Efficiency Expression Controlled By The $P_L$ Promoter of coliphage Lambda" *Gene*, 15:81–93) to absorb cross reacting antibodies from the diluted sera. Western blots and immunoassays were carried out according to methods described by Engvall, E. *Meth. Enzymol.* 70:419–439 (1980) and Hurn, B. A. L. and S. M. Chantler. *Meth. Enzymol.* 70:104–142 (1980).

Figure 4:
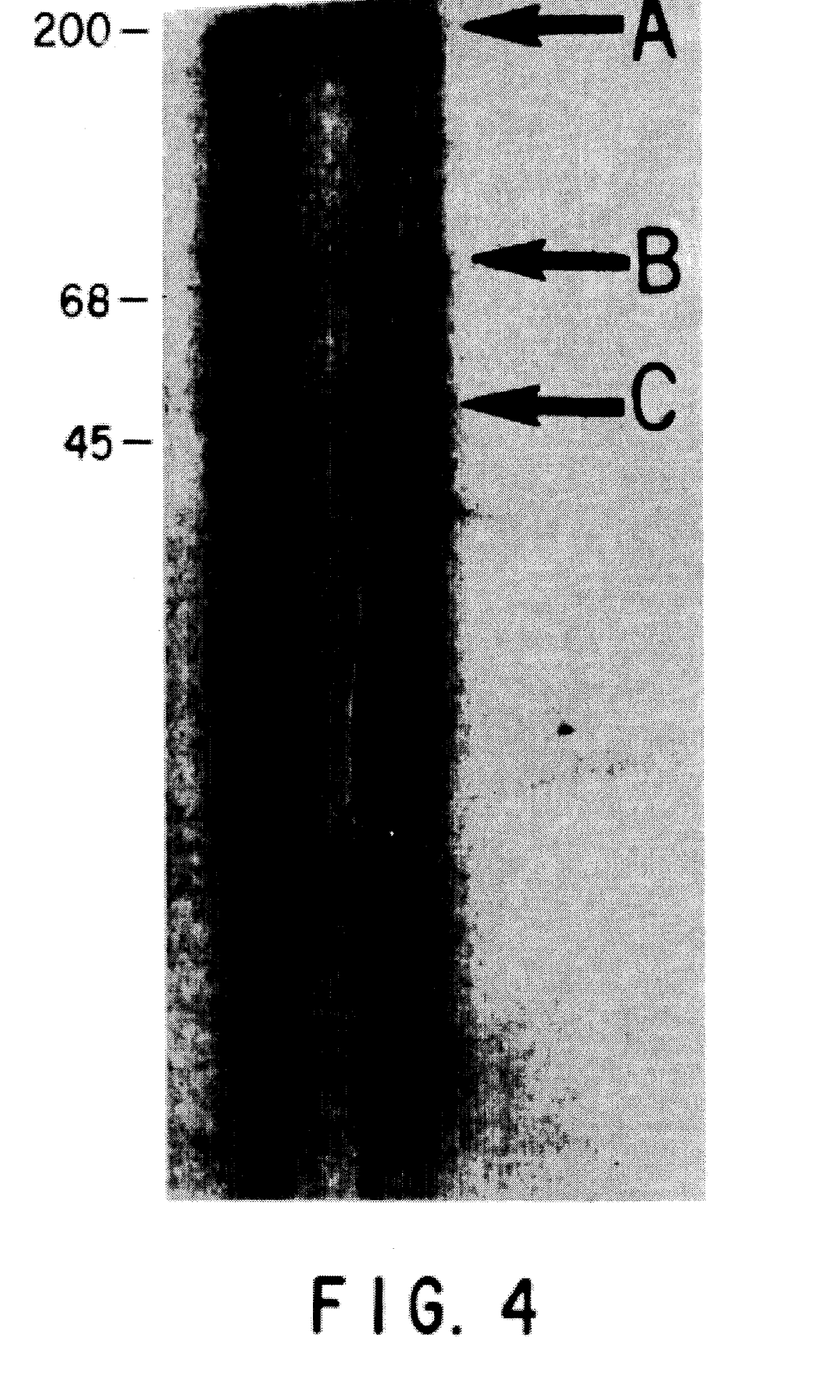
FIG. 4 shows Western blot analysis of the subunits of the major cellulases. This is a composite Western blot of subunits from the three major cellulases. A, about 90,000 dalton subunit of cellulase I; B: about 70,000 dalton subunit of cellulase II; C: about 50,000 dalton subunit of cellulase III.

Antibodies were produced against a mixture of these enzymes and a Western blot analysis revealed that the molecular weights of these enzymes I, II, and III were 90,000, 50,000 and 70,000, respectively, as shown in FIG. 4.

EXAMPLE 2(D)

Colorimetric Cellulase Assay.

Cellulase activity was determined by measuring the reducing sugars released by hydrolysis of pebble-milled cellulose. The reaction mixtures contained 0.05 ml of enzyme and 0.06 mg of pebble-milled cellulose in 0.5 ml of 0.05M phosphate, 0.05M NaCl, 0.02 ml toluene, and $10^{-3}$M 2-mercaptoethanol at pH 6.8 and were incubated for 24 h at 37° C. Control reaction tubes contained no enzyme. Undigested cellulose was removed by centrifugation, and the supernatant filtered through a 0.45 μm Millipore filter. Total carbohydrate produced was tested by the anthrone method as described above. Protein concentrations were determined by the Lowry method (Lowry, et al. *J. Biol. Chem.* 193:265–275 (1951)). The assay for β-galactosidase and the definition of enzyme unit were described by Miller (Miller, l. M. 1972. In: *Experiments in Molecular Genetics*. Cold Spring Harbor Laboratory Cold Spring Harbor, N.Y.).

EXAMPLE 3

Isolation, Cloning and Expression of the Clostridium Cellulase Gene in *E. coli*

(a) Isolation of Clostridium DNA.

Clostridium strain IY-2 was grown anaerobically (Hungate, R. E. 1969. "A roll tube method for cultivation of strict anaerobes", p. 117–139. In R. Norris and D. W. Ribbons (ed.), *Methods in microbiology*, *Vol. 3B*. Academic Press, Inc., New York) to early log phase in 1 L of CL medium containing 0.2% cellobiose. The cells were harvested by centrifugation, resuspended in 5 ml TE buffer (20 mM Tris-HCl, 0.2 mM EDTA, pH 7.6), and treated with 200 μg/ml proteinase K (Boehringer) plus 2% SDS at 37° C. for one hour. The crude chromosomal DNA-containing lysate was fractionated by centrifugation through a 10 to 40% sucrose gradient made with TES buffer (50 mM Tris-HCl, 5 mM ETA, 0.1M NaCl, 0.1% SDS) and DNA fragments larger than 15 kb were pooled. The DNA was extracted three times with phenol and precipitated with 2.5 volumes of ethanol. The DNA pellet was washed twice with 70% ethanol and dissolved in TE buffer and stored at 4° C.

(b) Cloning of Clostridium sp. DNA in Plasmid pLC2833.

Approximately 60 ug of purified Clostridium chromosomal DNA derived from the purified IY-2 strain and isolated as in Example 3(a) was digested with 2.6 units of Sau3A at 37° C. for 5, 10, 15, and 20 min. The size distribution of the partially digested DNA fragments was analyzed by 1% agarose gel electorphoresis. The fragments from 4 to 10 kb were pooled and used for shotgun cloning to form a plasmid herein referred to as pLC2833.

Plasmid DNA was prepared and purified by CsCl gradient centrifugation. The plasmid pLC2833 (Remault et al., supra) was digested with BamHI and dephosphorylated with calf alkaline phosphatase as described in Maniatis et al., *Molecular Cloning: A Laboratory Manual*. Cold Spring Harbor Laboratory, Cold Spring Harbor, N.Y. (1982). The partially Sau3A digested Clostridium strain IY-2 DNA fragments (6 μg) were ligated with 2 μg of BamHI digested pLC2833 DNA for overnight (12° C.) and then transformed into *E. coli* K-12. The *E. coli* K-12 strain was made competent and transformed by the procedures described by Remaut et al.

*Gene* 15:81–93 (1981). *E. coli* K-12 containing the plasmid pLC2833 (Remaut et al., supra) was grown in LB medium (10 g tryptone, 5 g yeast extract, 5 g NaCl, 2 g $MgCL_2$, per liter pH 7.4). Solid media contained 15 g agar per liter.

(c) Detection of Cellulase Positive Colonies.

The transformed *E. coli* cells were plated on LB agar plates containing 0.2% pebble-milled cellulose and 0.2% pebble-milled bamboo fibers, plus 75 µg ampicillin/ml. The plates were incubated at 28° C. for about 24 hours (replica plates were made) and then transferred to 37° C. for 48 hours. In the initial experiments the plates were exposed to chloroform for 2 min in order to lyse the cells and then incubated at 37° C. overnight. Colonies on the plate were washed off with sterilized $H_2O$, and 1% Congo red was used to stain the plates for several hours, the unbound stain was removed by washing with 1M NaCl solution. Clones producing cellulase were surrounded by a halo of clearing on a red background. Subsequently cellulase was found to be secreted from the *E. coli* cells and the chloroform treatment was not necessary.

(d) Results of Cloning and Expression of a Clostridium Cellulase in *E. coli*

The regulated high level *E. coli* expression vector pLC2833 (Remaut et al. *Gene* 15:81–93 (1981)) containing a $\lambda P_L$ promoter was initially chosen for the isolation of the Clostridium cellulase genes, because continuous high level production of cellulase may be detrimental to the host-vector system. The transcription from $\lambda P_L$ promoter is repressed at low temperatures and derepressed after shifting to 42° C. for one hour. The recombinant plasmids containing partially Sau3A digested Clostridium DNA fragments were transformed into *E. coli* K-12 and cellulase producing clones were isolated as described above. The results also revealed that cellulase activity was found whether the culture was grown at 28° C. or at 42° C. (Table 2). Thus the activation of the $\lambda P_L$ promoter was not necessary for the expression of the cellulase gene.

EXAMPLE 4

Restriction Endonuclease Mapping and Analysis of the Cloned Clostridium DNA Fragment Containing the Cellulase Gene.

The mapping method described by Danna K. J. 1980. *Meth. Enzymol.* 65:449–467 (1980) was used. The restriction enzymes Sau3A, AhaIII, HpaII, HindIII and EcoRI were used according to directions provided by Bethesda Research Laboratories. The recombinant plasmid pPC1 (plasmid pLC2833 containing a clostridrial insert (pPC1)) was isolated from *E. Coli* (pPC1). The BamHI site of pLC2833 into which the Sau3A fragment had been inserted was no longer susceptible to BamHI, but the BamHI site was flanked by unique EcoRI and HindIII sites. The insert was released by treatment of the plasmid with EcoRI and HindIII. This treatment revealed the presence of two fragments of 2.2 kb and 0.6 kb; thus the original pPC1 insert was approximately 2.8 kb.

Figure 5:
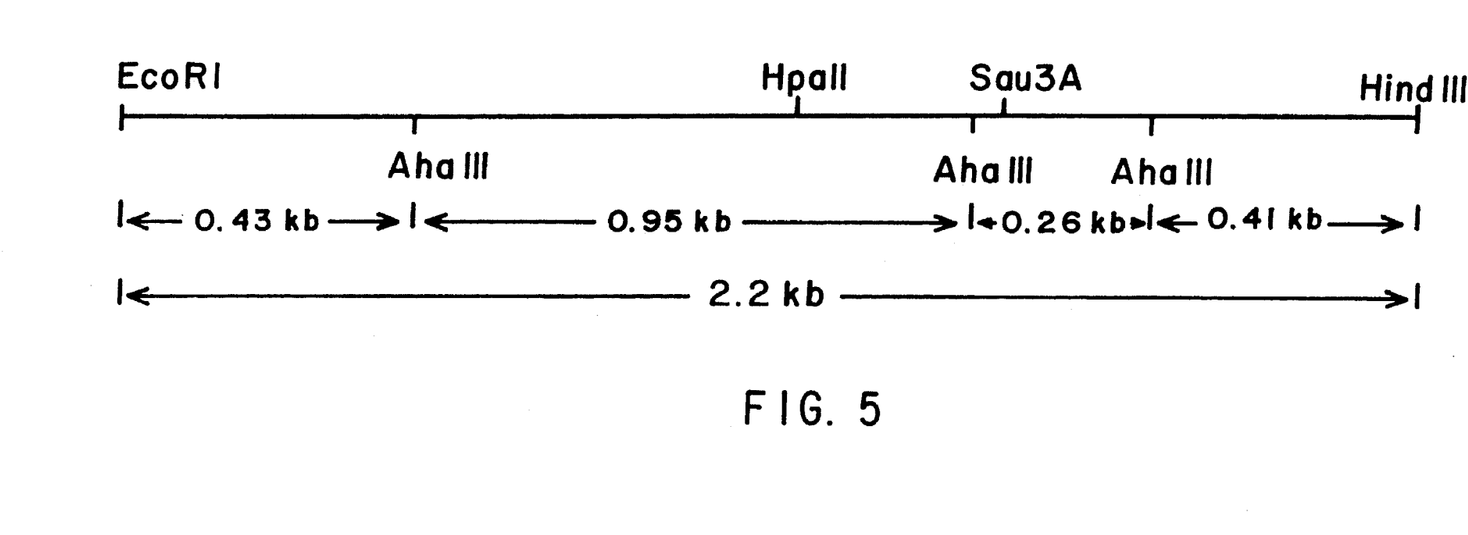
FIG. 5 is the restriction map analysis of the DNA fragment containing the cellulase gene.

The 2.2 kb EcoRI/HindIII fragment was gel purified and used for restriction mapping. The restriction map of this fragment is shown in FIG. 5. The fragment was cleaved by Sau3A, HpaII, and AhaIII, but not by BamHI, BclII, BglII, XhoII, AccI, TaqI, ClaI, HincII, PvuII, HpaI, DraI, RasI, SphI, PstI, SalI, XbaI, SmaI, KpnI or SstI.

Figure 6:
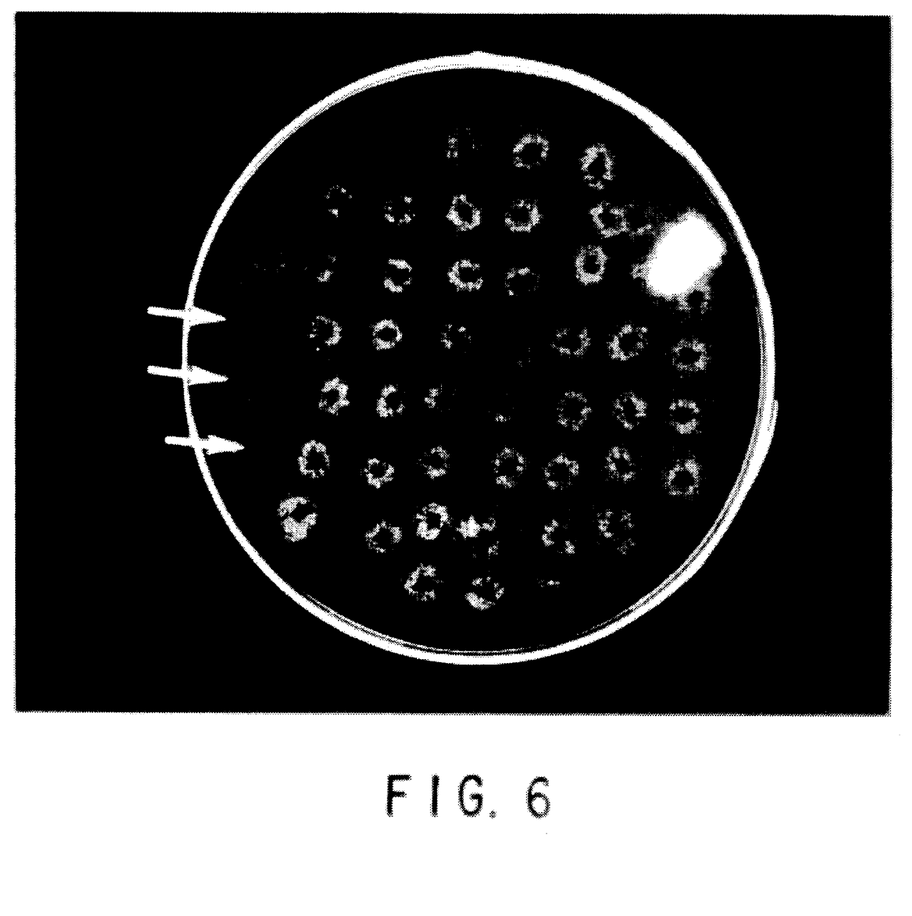
FIG. 6 shows halos (zones of cellulose hydrolysis) surrounding E. coli (pPC1A) colonies containing the cloned cellulase gene. The arrows point to the locations of E. coli colonies containing only the vector pLC2833 plasmid; no halos are apparent for these colonies.
Figure 7:
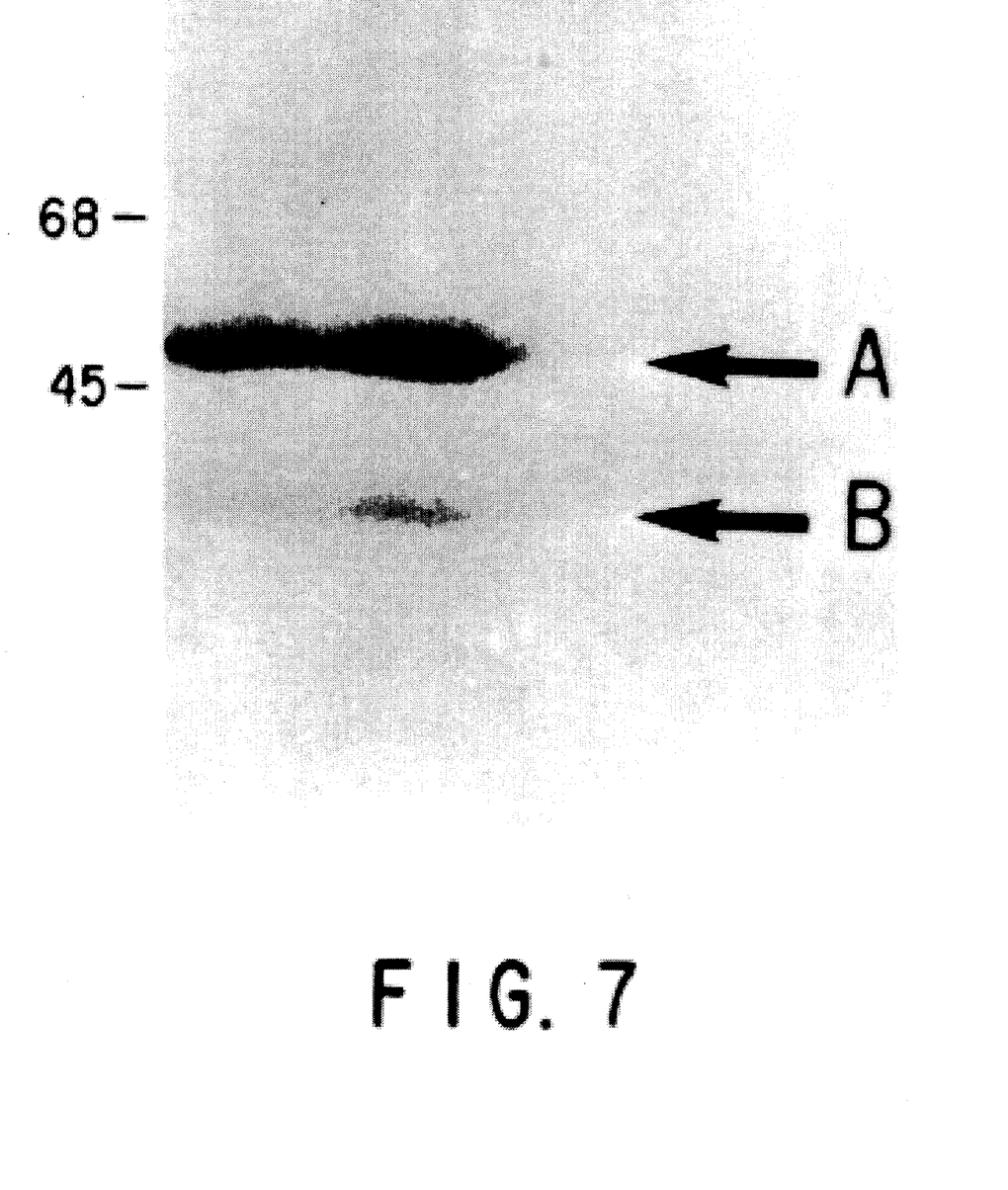
FIG. 7 shows Western blot analysis of the subunit from the enzyme produced from the cloned gene in E. coli. The MW of the subunit (A) is approximately 50,000 and (B) is the dye front. The numbers on the left indicate the molecular weight of standard proteins times $10^{-3}$.

The presence of the complete cellulase gene in this fragment was demonstrated by subcloning this 2.2 kb EcoRI/HindIII fragment (named fragment pPC1A) into the EcoRI-HindIII site which is downstream of the $\lambda P_L$ promoter of plasmid pLC2833 to produce plasmid pPC1A. The plasmid identified as pPC1A was deposited with the American Type Culture Collection having an accession number of 69,346 on May 14, 1993. *E. coli* transformants containing pPC1A were selected by screening for halo producing colonies on cellulose-agar plates (FIG. 6). These colonies were purified and were miniscreened for the presence of plasmid pPC1A. Plasmid pPC1A was found in all the cellulase producing clones analyzed and contained the 2.2 kb insert that was responsible for the cellulase activity. This was shown by growing *E. coli* transformants containing pPC1A in liquid cultures at 28° C. for 12 h and keeping part of the culture at 28° C. and shifting part of the culture to 42° C. for 4 hours before further growth at 37° C. The cell-free growth media of the *E. coli* transformants grown at 28° C. and at 42° C./37° C. both showed cellulase activity (Table 2, part c.). Western blot analysis with anti-cellulase antiserum showed the presence of the 50,000 dalton subunit from cellulase II only in the cell-free growth medium and not in the cell extracts (FIG. 7). This fragment PC1A contains the whole structural gene for the 50,000 dalton Clostridium sp. cellulase and, since the gene can be expressed well at 28° C. without shifting to 42° C., the cellulase gene may contain its own promoter or other promoter-like sequence that is recognized by the *E. coli* RNA polymerase.

The cellulase produced by *E. coli* was used to hydrolyze cellulose and the products formed were identified by thin layer chromatography as cellotetraose and soluble residues.

EXAMPLE 5

Analysis of Cellulase Products Following Cellulase Digestion

The cellulase products were analyzed by thin layer chromatography. Twenty gram of silica gel B (Brinkman Instrument, Inc.) was mixed with 40 ml of deionized water and immediately poured on a Kontes Plate (0.25 cm thickness) and air dried. One ml of enzyme reaction mixture was clarified by centrifugation, passed through a 0.45 µm or 8 µm Millipore filter, and desalted with Amberlite Anion exchange resin R-46 (OH), followed by cation exchange resin R-120. This desalted solution of the soluble products of digested cellulose was lyophilized. The dried residue was dissolved in 0.1 ml deionized water, and 1 to 5 µl were spotted on a silica plate. The chromatographic solvent used was n-propanol:ethyl acetate:$H_2O$ (7:1:2). After the solvent had moved to the top of the plates, the plates were air dried. The spots were detected by spraying with a warm anthrone solution (300 mg anthrone, 10 ml acetic acid, 20 ml ethanol, 3 ml $H_3PO_4$ and 1 ml $H_2O$), followed by heating at 65° C. for 10 min. Fifty percent (v/v) $H_2SO_4$ also was used as a spray reagent, followed by heating in a 65° C. oven for 30 min.

Cellulase activity was recovered and characterized based on the cellular location as extracellular, periplasmic and intracellular cellulase activity. The "extracellular" enzyme is defined as the sum of the enzyme activity in the cell-free culture fluid. Osmotic shock was performed as described by Neu and Heppel *J. Biol. Chem.* 240:3685–3692 (1965) to obtain cellulase located in the periplasmic space. The "periplasmic" enzyme is the activity found in the supernatant fraction after cold shock treatment of cells. The "intracellular" enzyme was obtained by subjecting cold shocked cells to sonic oscillation and measuring the enzyme activity in the cell free extract.

Since halos were produced around the transformed *E. coli* clones on the cellulose-containing plates even in the absence of chloroform treatment, it is suggested that there is a possibility that the cellulase was being secreted from the cell. The cellular location of the cellulase was tested by growing one of the transformants, *E. coli* (pPC1), in a liquid culture and testing for cellulase in the culture supernatant, in the periplasmic space, and in the cell extract. Essentially all the cellulase activity was present in the supernatant of the growth medium and no activity could be detected in the cellular extract (Table 2, part b.) nor in the periplasmic space (Table 3). As a control β-galactosidase activity was also measured concurrently with the cellulase (Table 3). The β-galactosidase activity was found primarily in the intracellular extract during growth and some activity was found in the periplasmic space in the stationary phase; however very little activity (less than 10%) was found in the supernatant while more than 90% of the cellulase activity was present in the intracellular fraction. Western blot analyses of the cell extract and supernatant of the cultures revealed that almost all the cellulase was in the supernatant fraction (Table 3). Thus it proves that the cellulase is secreted from *E. coli* and the presence of cellulase in the culture medium is not the result of lysis of the cells. While there have been previous reports of heterologous proteins being secreted into the medium by *E. coli* (Abrahamsen et al. *Nucl. Acid Res.* 14:7487–7500 (1986)), the secretion of high levels of functional cellulase by *E. coli* may provide great utility for the production of extracellular cellulase.

Western blot analysis of the supernatant with anti-cellulase antibody revealed the presence of a protein with a MW of 50,000 which is the MW of the subunit from cellulase II produced by the Clostridium sp. (FIG. 4). The results also revealed that cellulase activity was found whether the culture was grown at 28° C. or at 42° C. (Table 2). Thus the activation of the λP$_L$ promoter was not necessary for the expression of the cellulase gene. Since the cellulase activity and the protein reacting with anti-cellulase antibody were absent from control cells containing pLC2833 (Table 2, part a.), the results strongly indicated that the recombinant plasmid contained a Clostridium cellulase gene that was expressed constitutively in *E. coli* and that the product was secreted into the medium.

TABLE 2

Localization of Cellulase in *E. coli* Cells Containing the Cloned Clostridium sp. Gene

| Source of Enzyme | Glucose Produced (mg/ml) | Protein MW |
|---|---|---|
| a. *E. coli* (pLC2833) | | |
| culture medium (28° C.) | 0.1 | None |
| culture medium (42° C.) | 0.1 | None |
| cell extract (28° C.) | 0.1 | None |
| cell extract (42° C.) | 0.1 | None |
| b. *E. coli*. (pPCl) | | |
| culture medium (28° C.) | 1.5 | 50,000 |
| culture medium (42° C.) | 1.3 | 50,000 |

TABLE 2-continued

Localization of Cellulase in *E. coli* Cells Containing the Cloned Clostridium sp. Gene

| Source of Enzyme | Glucose Produced (mg/ml) | Protein MW |
|---|---|---|
| cell extract (28° C.) | 0.1 | None |
| cell extract (42° C.) | 0.1 | None |
| c. *E. coli* (pPClA) | | |
| culture medium (28° C.) | 1.1 | 50,000 |
| culture medium (42° C.) | 1.4 | 50,000 |
| cell extract (28° C.) | 0.2 | None |
| cell extract (42° C.) | 0.1 | None |

TABLE 3

Localization of β-galactosidase in *E. coli* Cells with Recombinant Plasmids

| | Total Enzyme Activity | |
|---|---|---|
| Source of Enzyme | galactosidase units | Cellulase mg glucose/ml$^b$ |
| *E. coli* + pLC2833 | | |
| cytoplasm | 118.7 (59.6%) | trace |
| periplasmic space | 71.7 (36.0%) | trace |
| culture supernatant | 8.7 ( 4.4%) | trace |
| *E. coli* + pPClA | | |
| cytoplasm | 92.1 (76.4%) | 0.6 ( 0.9%) |
| periplasmic space | 16.8 (13.9%) | 3.6 ( 5.6%) |
| culture supernatant | 11.7 ( 9.7%) | 60.0 (93.5%) |

Description of Deposits

The transformed bacterium, *E. coli* k-12, which contains a plasmid (pPC1A) that carries a cloned Clostridium strain IY-2 DNA fragment coding for the 50,000 dalton Clostridium cellulase was deposited with the American Type Culture Collection on May 14, 1993, and has Accession Number ATCC 69,346. The novel, purified and isolated strain identified as IY-2 was deposited with the safety collection of the American Type Culture Collection on Apr. 1, 1989 as ATCC Number 1227.

The invention now being fully described, it will be apparent to one of ordinary skill in the art that many changes and modifications can be made thereto without departing from the spirit or scope of the invention as set forth herein.

I claim:

1. A recombinant microorganism comprising a vector for the heterologous expression of a cellulase enzyme wherein said enzyme is capable of digesting chemically or enzymatically untreated natural plant materials and said enzyme has a molecular weight of about 58,000 daltons as measured by gel exclusion chromatography wherein said microorganism comprises:

(a) an expression vector comprising a DNA sequence coding for said cellulase enzyme; and (b) at least one DNA sequence coding for a signal sequence useful for the secretion of said cellulase enzyme, wherein a first DNA sequence of the expression vector codes for cellulase obtained from Clostridium strain IY-2.

2. A microorganism of claim 1 wherein the expression vector is an *E. coli* plasmid, pLC2833, containing a $\lambda P_L$ promoter and a 2.8 kb Clostridiim strain IY-2 DNA insert.

3. A microorganism of claim 2 wherein said 2.8 kb insert is further cleaved into 2.2 kb DNA fragment comprising at least an entire structural gene and signal sequences of cellulase and the promoter is from the Clostridium cellulase gene on plasmid pPC1A.

4. A microorganism of claim 3 wherein the 2.2 kb DNA fragment is subcloned into a plasmid, pPC1A, containing a $\lambda P_L$ promoter derived from pLC2833.

5. A microorganism of claim 4 wherein the microorganism is *E. coli* k-12.

* * * * *